United States Patent
Peltie et al.

(10) Patent No.: US 6,510,237 B1
(45) Date of Patent: Jan. 21, 2003

(54) SYSTEM FOR DETERMINING THE CONCENTRATION OF A SUBSTANCE MIXED WITH A FLUOROPHOR, ITS METHOD OF IMPLEMENTATION

(75) Inventors: Philippe Peltie, St Paul de Varces (FR); Dominique David, Claix (FR)

(73) Assignee: Commissariat a l'Energie Atomique, Paris (FR)

(*) Notice: Subject to any disclaimer, the term of this patent is extended or adjusted under 35 U.S.C. 154(b) by 0 days.

(21) Appl. No.: 09/418,518

(22) Filed: Oct. 15, 1999

(30) Foreign Application Priority Data

Oct. 27, 1998 (FR) .......................................... 98 13438

(51) Int. Cl.$^7$ ................................................. G06K 9/00
(52) U.S. Cl. .......................... 382/128; 378/42; 378/45
(58) Field of Search ..................... 378/42–45; 382/128, 382/129

(56) References Cited

U.S. PATENT DOCUMENTS

| | | | | |
|---|---|---|---|---|
| 4,884,881 A | * | 12/1989 | Lichtman et al. | 359/227 |
| 4,962,516 A | * | 10/1990 | Soezima | 250/307 |
| 5,252,834 A | | 10/1993 | Lin | |
| 5,323,009 A | * | 6/1994 | Harris | 250/227.2 |
| 5,430,786 A | * | 7/1995 | Komatsu et al. | 378/45 |
| 5,479,252 A | | 12/1995 | Bruce et al. | |
| 5,521,755 A | * | 5/1996 | Stankewitz | 359/385 |
| 5,721,759 A | * | 2/1998 | Raatikainen | 378/44 |
| 5,734,498 A | * | 3/1998 | Krasieva et al. | 359/368 |
| 5,813,987 A | * | 9/1998 | Modell et al. | 250/216 |
| 5,943,129 A | * | 8/1999 | Hoyt et al. | 250/458.1 |
| 6,169,289 B1 | * | 1/2001 | White et al. | 250/458.1 |
| 6,345,115 B1 | * | 2/2002 | Ramm et al. | 377/10 |
| 6,403,957 B1 | * | 6/2002 | Fodor et al. | 250/302 |

FOREIGN PATENT DOCUMENTS

| | | |
|---|---|---|
| EP | 0 160 568 | 11/1985 |
| WO | WO 98/38490 | 9/1998 |

OTHER PUBLICATIONS

Michel Bellis, et al., Médecine Sciences, vol. 13, No. 11, pp. 1317–1324, "La Puce Adn: Un Multi–Réacteur De Paillasse", 1997.

* cited by examiner

*Primary Examiner*—Joseph Mancuso
*Assistant Examiner*—Anand Bhatnagar
(74) *Attorney, Agent, or Firm*—Oblon, Spivak, McClelland, Maier & Neustadt, P.C.

(57) ABSTRACT

The invention concerns a system, and its method of implementation, to determine the concentration of a substance mixed with a fluorophor and contained in one or more contacts of a matrix of contacts; it comprises:

Figure 1:
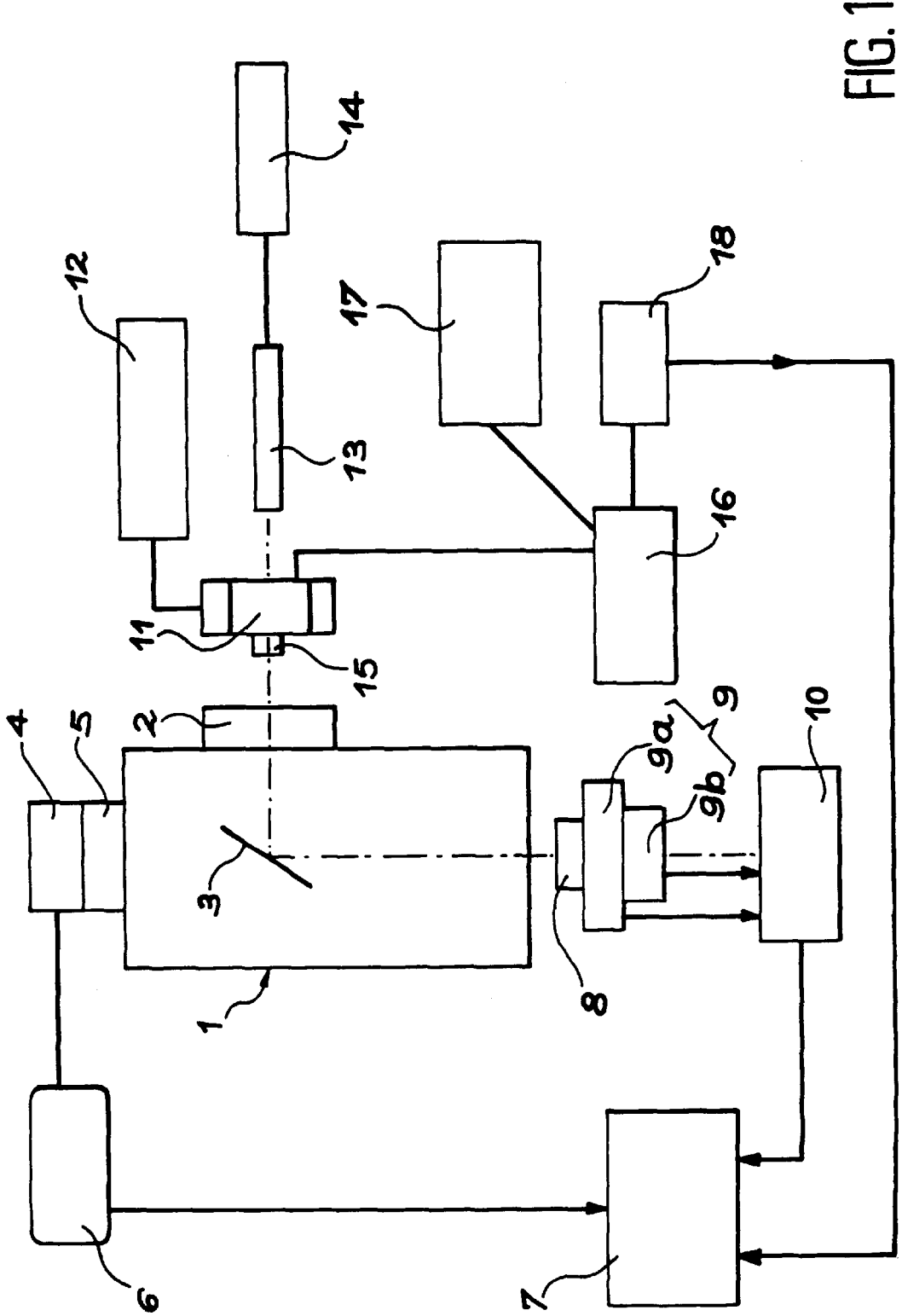

- a microscope (1) associated with a magnifying objective lens (2) and with image acquisition means (4,5) to achieve a microscope image of the fluorescence of one of the contacts of the matrix or part of this contact;
- illumination means (11, 13) emitting a first beam to enable image acquisition in white light of said contact, and a second beam to excite the fluorophor contained in said contact;
- deflector means (15) for the second beam to ensure point by point scanning of the contact of the matrix;
- recording means (6, 7) to record the contact image; and
- processing means (6,7) of this image to quantify the fluorescence of the contact and determine the concentration of the substance.

17 Claims, 3 Drawing Sheets

SYSTEM FOR DETERMINING THE CONCENTRATION OF A SUBSTANCE MIXED WITH A FLUOROPHOR, ITS METHOD OF IMPLEMENTATION

FIELD OF THE INVENTION

The invention concerns a system to determine the concentration of a substance mixed with a fluorophor; it also relates to its method of implementation.

The invention finds applications in numerous areas, in particular in the medical field for genome sequencing, the identification of mutations responsible for genetic diseases, the development of new medicinal products, etc.

STATE OF THE ART

Fluorescence (or short-lived photoluminescence) is a selective chemical analytical technique often used by persons skilled in the art to determine the concentration of a substance. The substance to be examined is mixed with a fluorophor. The fluorophor molecule, when excited at a wavelength $\lambda$, has the property of re-emitting light with a spectrum whose maximum is greater than the emitted wavelength ($\lambda'>\lambda$; STOKES' law). As soon as excitation is stopped, fluorescence decreases exponential fashion : $It=I_o*e^{-kt}$. Therefore, to observe a "remanent" fluorescence phenomenon, excitation needs to be maintained.

Also, it is known that not all the energy stored by the molecule is released in fluorescence form. The molecule maintains some of the energy in the form of vibration. This excess energy is dispelled by non-radiating processes called vibration relaxation mechanisms.

It is therefore possible to determine the fluorescence yield $\rho$, which is the ratio between the number of emitted photons and the number of absorbed photons; this yield is $\rho=If/Ia$.

It is shown that $If=\rho*I_o*\epsilon*l*C$ in which $I_o$ is the exciting intensity, l is the thickness of the substance, C is the molar concentration and $\epsilon$ is the molar absorption coefficient of the substance.

On the other hand, if the concentration increase is too great, fluorescence is no longer proportional to concentration as the solution absorbs quicker than its fluoresces. In this case the limits of the "linear zone" are exceeded.

If a CCD camera is positioned to form the fluorescence image, it can be said as a first approximation that the illumination received by the camera is proportional to If, fluorescence being isotropic in space; the situation is then $E=\pi*L*d\Sigma/dS$ (LAMBERT's law), in which E is the illumination, L is the luminance (constant for isotropic emission and proportional to excitation intensity), $d\Sigma$ is the emitter surface, and dS is the CCD pixel surface. However, the video signal leaving the camera is given by the ratio: $Vos=q*\eta*Nph*G/Cl$, in which q is the electric charge, Nph is the number of incident photons, G is the gain, Cl is outgoing capacity and $\eta$ is the quantum yield.

If the CCD camera is not saturated, illumination is proportional to integration time and to the number of photons received per time unit. It can then be written that Vos is proportional to the intensity of fluorescence If and integration time T, hence to the intensity of excitation $I_o$, to integration time T, and to the molar concentration, the other parameters being fixed and dependent upon the instruments used; i.e.: $Vos=k*I_o*T*C*$.

This formula is true if, and only if, work is conducted in a linear zone, that is to say if the molar concentration is not too high, if the excitation intensity does not cause absorption which would mask fluorescence, and if emission intensity and integration time do not saturate the CCD camera.

Therefore if it is desired to quantify fluorescence, it is essential to calibrate the experiment having the possibility of acting on two factors; integration time and the intensity of the excitation laser. This calibration may be made for example using contacts coated with a substance of known concentration. With a camera cooled to a very low noise level, it is possible to imagine that a resolution of 10 bits can be obtained, that is to say dynamics of 1000 or even more.

This fluorescence technique is used in particular for the identification and titration of the constituents of a DNA mixture applied to the surface of nucleic acid chip, called a DNA chip. The titration of the constituents of this mixture is made by using a DNA chip reader.

There currently exist numerous DNA chip readers, each adapted to a particular type of chip.

Documents U.S. Pat. No. 5,578,832, WO-97 4361 and U.S. Pat. No. 5,646,411 for example describe reading systems adapted to the chip produced by AFFYMETRIX, called the GENECHIP®. Each of these systems consists of a scanning microscope used in confocal or non-confocal mode for point-by-point analysis of a surface area of approximately 10×10 mm in steps of 10 to 50 $\mu$m.

Document U.S. Pat. No. 5,585,639 describes a linear strip reading system which provides sequential reading and reconstruction of a 2D image of chip fluorescence. This system is also adapted to the reading of GENECHIP® chips.

The size of the GENECHIP® is relatively large however for a chip, that is to say approximately 10×10 mm which is a disadvantage for some applications. Also, these chips comprise a high number of contacts, contiguous in both dimensions, which may make them difficult to localise. Finally, several contacts have to be read in order to achieve a biologically significant measurement.

DISCLOSURE OF THE INVENTION

The invention precisely discloses a reader that is adapted to another type of DNA chip, in particular to MICAM® chips which are of smaller size (1×2 mm²) with less numerous contacts (100 to 1000) which are well spaced out (100 $\mu$m). With this structure each contact is able to carry a well defined sequence that is perfectly well localised.

In other words, the invention concerns a system for determining the concentrations of the components of a mixed substance, for example containing DNA, applied to the surface of a MICAM® chip.

More precisely, the invention provides a system for determining the concentration of a substance mixed with a fluorophor and contained in one or more contacts of a matrix of conductor or non-conductor contacts positioned on a scarcely absorbent, reflective carrier characterised in that it comprises:

a microscope associated with a magnifying objective lens, and with image acquisition means to acquire a microscope image of the fluorescence of one of the contacts of the matrix or part of this contact;
  illumination means emitting a first beam to allow image acquisition in white light of said contact, and a second beam to excite the fluorophor contained in said contact;
  means for deflecting the second beam to ensure point by point scanning of the contact of the matrix;
  means for recording the contact image and
  means for processing this image to quantify the fluorescence of the contact and to determine the concentration of the substance mixed with the fluorophor, using fluorescence intensity, illumination intensity and integration time on the image acquisition means.

Advantageously, the illumination means comprise a ring illumination source which emits the first beam and a laser source which emits the second beam.

According to one embodiment of the invention, the image acquisition means comprise a cooled CCD camera, a colour filter placed in front of said camera and an electronic circuit ensuring the piloting of the photo multiplier and illumination means.

According to another embodiment of the invention, the image accusation means comprise a photo multiplier associated with an acquisition circuit, a colour filter placed in front of said photo multiplier and an electronic circuit ensuring the piloting of the camera and illumination means.

The microscope of the system of the invention my be fitted with a dichroic filter.

Advantageously, this microscope operates under epi-illumination.

Preferably, the deflector means of the system of the invention consist of an acoustic optical deflector deflecting the second beam in two orthogonal directions X and Y.

According to one embodiment of the invention, the laser is a micro laser; this may be a pulsated micro laser.

According to one variant of the invention, the colour filter is a high-pass filter.

In some applications, the matrix is an electrically-addressable matrix.

Also, the substance may be made up of DNA strands hybridised to probes made from synthesised DNA, and these DNA probes may be strongly fixed to the contacts with polypyrrol.

Depending upon the application, the fluorophor may be phycroerythrine, C-Snarf or sulphorhodamine, or any other fluorescent substance.

According to one embodiment, the system forms a reading box of small size and the contact matrix is carried on a card of "chip card" type.

The invention also concerns the method of implementing the above system which is characterised in that it consists of:
   a system calibration step with positioning and blocking of the matrix underneath the optical axis of the microscope objective, focusing the image acquisition means and automatic search of a reference contact in relation to the optical centre of the system;
   an image acquisition step of one contact of the matrix; and
   a calculation step of the fluorescence of said contact and subsequent deduction of the concentration of the substance.

In the embodiment in which image acquisition is made using a cooled CCD camera, the method of the invention comprises, between the calibration and acquisition steps, a scanning step with point by point scanning of the contact under consideration.

Short Description of the Figures

FIG. 1 shows a diagram of the system of the invention; and

Figure 2A:
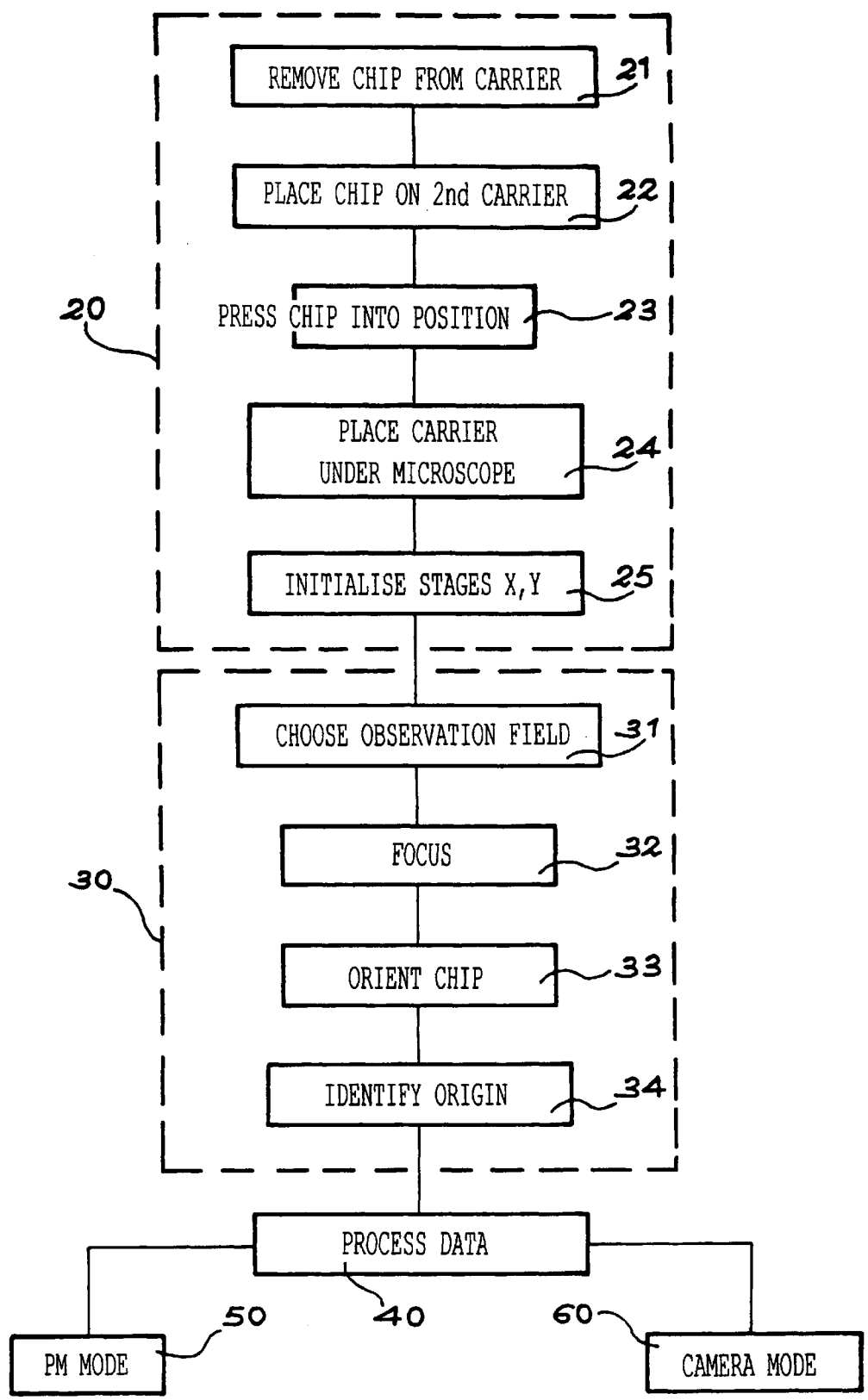
Figure 2C:
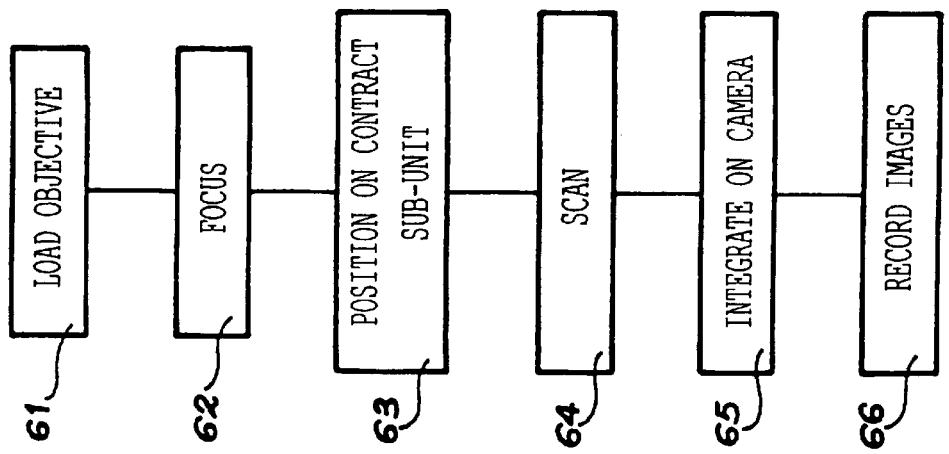
Figure 2B:
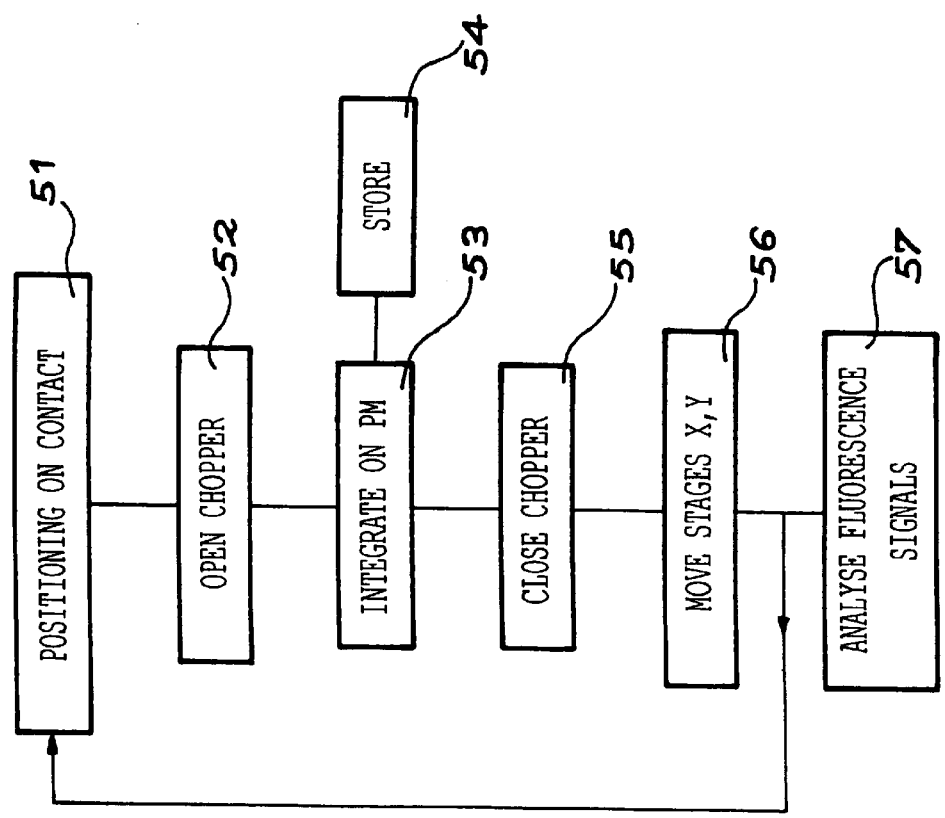

FIGS. 2A, 2B and 2C give a functional diagram of the method for implementing the system of the invention.

DETAILED DESCRIPTION OF THE EMBODIMENTS OF THE INVENTION

The invention concerns a system for determining the concentration of a substance mixed with a fluorophor and contained in one or more contacts of a matrix of contacts arranged on a scarcely absorbent, reflective carrier. The fluorophor is generally chosen from among the following products: phycoerythrine, C-Snarf or sulphorhodamine.

This system comprises a microscope which preferably operates under epi-illumination, that is to say by light reflection, associated with an objective which may magnify up to five, ten, twenty times etc., and image acquisition means intended to acquire a through-microscope image of the fluorescence of one of the matrix contacts or of part of a contact.

The system also comprises illumination means which preferably consist of a first ring illumination source which emits a first light beam, and a laser source which emits a second light beam. The first beam is used to acquire an image in white light of the contact being studied, and the second beam is intended to excite the fluorophor contained in the mixture of substances.

The system of the invention also comprises deflector means intended to deflect the second beam and to ensure point by point scanning of the contact or part of the contact to be examined.

It also comprises means for recording the image of the contact and processing means to analyse this image, in order to quantify the fluorescence of the contact and hence determine the concentration of the substance mixed with the fluorophor.

As will be seen in more detail below, the image acquisition means may consist of a cooled CCD camera in front of which a colour filter is placed. This camera is associated with an electronic circuit which ensures the piloting of the camera and illumination means.

According to another variant, the image acquisition means may consist of a photo multiplier associated with an acquisition circuit in front of which a colour filter is placed; an electronic circuit associated with this photo multiplier ensures the piloting of the latter and piloting of the illumination means.

The system of the invention previously described in general manner may be used in particular to determine the concentration of a substance mixed with a fluorophor and applied to the contacts of an electrically addressable matrix, such as a DNA chip. In this case, the substance to be analysed is generally a substance made up of DNA strands hybridised to probes made of synthesised DNA. The DNA probes can be made to adhere strongly to the contacts using polypyrrol.

The system particularly applies to the MICAM® chip.

It is this embodiment relating to the MICAM® chip which will be described in detail in the remainder of this disclosure.

The MICAM® chip is of limited size (approximately 2×2 mm$^2$) and comprises approximately 100 to 1000 contacts measuring about 50 µm each and well spaced out from one another, that is to say distanced by approximately 100 µm. Contact numbering exactly follows probe graft numbering, namely BOUSTROPHEDON type numbering.

With this structure it is possible for each contact of the chip to carry a well defined sequence which illustrates what the operator sets out to find, that is to say biological information. This MICAM® chip also has the advantage of enabling perfect localisation of each probe embedded in the chip contacts. For example, when identifying the mutation of some codons in a given gene, that is to say in what biologists call "resequencing", the probe which will respond to this search, that is to say the probe on which one or more DNA sequences will attach themselves, can be fully localised. The biologist therefore has available a very precise map on which points of particular interest can be located for quantification.

Also, the system of the invention has the advantage of providing biologists with a global image of the chip through the microscope. This association of a "very precise contact map" and "through-microscope image" offers biologists the opportunity to extract the information of interest at the exact point where it is located by means of random access scanning with a laser beam.

The term "random scanning" is applied to the possibility of acquiring an image in white light and, by means of a deflector, to instantly address a laser beam to any point in the field. This so-called "random" scanning offers the possibility of working under epi-illumination, or under an incidence of approximately 45° (and more generally between 30 and 60°). This provides a considerable time saving and a gain in memory since only the contacts of interest to the biologist are addressed. However it will be observed that said random scanning, while it may be used with a MICAM® chip which has non-contiguous contacts, it cannot be used with most chips and in particular with so-called GENECHIP® chips as the sequences are fragmented into side by side elements and scanning is necessarily sequential.

However, under experimental conditions there may be only a few contacts of interest for examination, therefore random access scanning offers great advantages if only through its rapidity and the elimination of useless zones, that is to say contacts considered of no interest by the biologist.

To conduct random access scanning, a scanning microscope is used since, as explained in the study by T. WILSON "Theory and practice of scanning optical microscopy", 1984, a scanning microscope makes it possible to concentrate energy on one contact to be analysed and to scan the surface of this contact point by point; in this way stray light is greatly reduced since only the illuminated point is fluorescent. This scanning microscope therefore offers both accurate impulse response and high quality performance.

According to the preferred embodiment of the invention, this scanning microscope is obtained from a conventional microscope associated with deflector means, such as for example an acoustic optical deflector, which conducts laser scanning in 10 μm steps over a field of 2.5 mm through the microscope objective lens and in two orthogonal directions X and Y. With this type of system, random access scanning is obtained with an access time in the region of a few μs.

Taking into account the small size of the MICAM® chip, acoustic optical-type scanning is advantageous; however other types of scanning, for example galvanometric mirror scanning, or travelling stage scanning may also be used.

Also, given the small size and particular structure of the MICAM® chip, it is not necessary to work in confocal mode It is recalled, if need be, that the term "confocal" means that, via spatial filtering techniques, a small reading volume can be isolated whose size essentially depends on the digital opening of the objective. For example, for a MICAM® chip, a 10× objective can be used, that is to say having a digital aperture of DA=0.25, which gives a confocal volume with a diameter of 1 μm for a height of 8 μm. The size of the contacts of a MICAM® chip however is about 50 μm, which needs to be viewed with defocusing of less than 10 μm. It is therefore not necessary to use the confocal mode.

FIG. 1 gives a diagram of the system of the invention adapted for the reading of MICAM® chips.

This system comprises a conventional microscope, denoted 1, intended to operate under epi-illumination, that is to say by reflection. An objective lens 2 is fixed to microscope 1; this objective may have a power of magnification of 5× or 10× or 20×. The most conventional objectives are:
5× objective: DA=0.10;
 adjusted to infinity;
 f=approximately 35 mm;
10× objective, achromatic plane: DA=0.30:
 adjusted to infinity;
 f=approx. 16 mm;
 this lens gives a working distance of 10 mm with a resolution of 1.12 μm,
20× objective, achromatic plane: DA=0.46;
 adjusted to infinity;
 f=approx. 8 mm;
 the working distance is 3 mm and resolution is 0.73 μm.

It is also possible to use a 50× objective but its working distance is short, i.e. 1 mm; it cannot be used therefore on a glass-covered conventional chip.

According to the embodiment shown in FIG. 1, microscope 1 is fitted with a dichroic filter 3, which may differ according to the type of laser used.

Also, microscope 1 is used in conjunction with image acquisition means which, in this embodiment, consists of a camera denoted 4.

Preferably this camera is a CCD camera cooled to between 0 and −20° C. This camera 4 is associated with an electronic circuit which ensures the piloting of the camera and of the illumination means which will be described more in detail below. This electronic circuit denoted 6, ensures the transfer of information derived from the system towards computer means, denoted 7 in FIG. 1. These computer means may quite simply be a PC.

Also, the image acquisition means comprise a filter 5, placed in front of the detector. This filter 5 is a colour filter, preferably orange, whose role is to prevent Rayleigh-type retrodiffusion, that is to say retrodiffusion of fluorophor excitation light. Advantageously filter 5 is a high-pass filter with a cut-off frequency of approximately 550 nm.

As seen in this figure, the microscope is placed above the MICAM® chip, denoted 8, itself placed on a travelling stage 9. This travelling stage may be a set of two travelling stages, one travelling horizontally along the X axis and the other moving perpendicularly along the Y axis. These stages X and Y may be manual. According to the embodiment shown in FIG. 1, these two stages denoted 9a and 9b respectively, are motorised and connected to the PC 7 by controls 10. In addition to its movements along axes X and Y, stage 9 may also be oriented in rotation according to an angle θ, by means of a micrometric platform operated manually or automatically depending on the embodiment chosen.

The system of the invention also comprises illumination means intended firstly for image acquisition and secondly for fluorophor excitation. These image acquisition means comprise ring illumination means 11 made of several white electro luminescent diodes, distributed over a ring-shaped carrier and piloted by a low voltage power source, i.e. 10 to 20 V, denoted 12. This ring illumination 11 is intended to be used for the white light acquisition of an image of the chip or part of the chip.

This ring illumination means 11 is piloted by a driver (or control device) 61, itself supplied by a power source 17 whose polarisation voltage is for example 24 V with a modulation voltage of 5 V. Driver 16 is also connected to a programmable power source which supplies a deflection voltage varying between 0 and 10 V, itself piloted by PC, 7.

The illumination means also comprise a laser source 13, supplied by a power source 14 emitting a laser beam intended to excite the fluorophor contained in the mixture. The laser beam emitted by laser source 13 is deflected in two orthogonal directions X and Y by an acoustic optical deflector, denoted 15.

This laser may be a polarised green HeNe laser or an argon laser. This laser 13 may also, according to the embodiment chosen, be a continuous or pulsated micro laser.

Therefore with the system shown in FIG. 1, the image of the chip is formed through the 5× or 10× objective. The 5× objective covers approximately 2.3×1.5 mm$^2$, that is to say all the surface of a MICAM® chip; the 10× objective covers approximately 0.7×0.5 mm$^2$, that is to say approximately one quarter of the field since the active part of the MICAM® chip measures 1.6×0.8 mm$^2$.

With a 10× objective, the system operates as follows: the laser, preferably a green HeNe laser, emits a beam which is magnified four times to enter into acoustic optical deflector 15 with a diameter of 3.52 mm and a divergence of 0.2 mrad. With this 10× objective, scanning of approximately 16 mm×41 mrad is obtained in the object plane, that is to say approximately 700 μm which corresponds to the field seen by the CCD camera. It is then possible either to scan the contact to be analysed point by point, or to scan the entire contact and leave the camera to integrate the different images for a certain time period, for example 1 s.

In the particular case when the contact to be scanned is 50×50 μm, that is to say 3.12 mrad along each axis, a voltage step of 0.75 V is obtained. In this case a voltage ramp on each of axes X and Y is made from an angle θo up to θo+3.1 mrad. With a recurrence frequency of 1 kHz, the to and fro movement of the laser beam is made in 8 μs at a level of ⅓, i.e. a step of 2 μs along the other axis. In this case 25 return movements are needed, that is to say 25 μs to scan all the contact. For an integration time of 1 s which is the average integration time for a CCD camera, it is therefore possible to conduct 40 scannings.

With a 5× objective, a beam with a divergence of 0.8 mrad is obtained which, for a focal length of 40 mm, gives scanning in the object plane of approximately 32 μm. The integration of the contact images is therefore made between 0.5 s and 1 s. The step distance of the acoustic optical deflector is 100 μm and the field scanned is approximately 1.64 mm. The angular step of scanning is 2.5 mrad, which corresponds to a voltage variation ΔV of 0.61 V.

As previously seen, the system of the invention preferably comprises a microscope operating under epi-illumination, that is to say in which scanning is made by reflection through the microscope objective.

However, it is also possible to excite the fluorophor by means of a HeNe laser and an optical lens whose optical axis lies between 30 and 60° incident to the vertical direction. This embodiment is less easy to implement than the epi-illumination embodiment, but it has the advantage of eliminating all stray reflections that is to say the incident light reflected outside the objective (approximately 30% of incident light).

The system of the invention just described is implemented using a method which consists of:
- a system calibration step with positioning and blocking of the matrix under the optical axis of the microscope, focusing of the image acquisition means and automatic search of a reference contact in relation to the optical centre of the system;
- an image acquisition step of a contact of the matrix; and
- a calculation step to calculate the fluorescence of said contact, then deduction of the concentration of the substance.

In the event that image acquisition is made using a cooled CCD camera, the method comprises, between the calibration and image acquisition steps, a point by point scanning step of the contact on which a substance is applied whose concentration needs to be determined.

FIGS. 2A, 2B and 2C give a functional diagram of the method of the invention with two modes of information processing, namely the mode used when the acquisition means consist of a photo multiplier associated with an acquisition circuit, and the one in which the image acquisition means consist of a cooled CCD camera.

FIG. 2A shows the steps of the implementation method for the reader of the invention, which are common to both embodiments, that is to say the embodiment in which the image is made by means of a photo multiplier associated with an acquisition circuit, called "PM mode" and the embodiment using a CCD camera called "CAMERA mode".

This method entails three main parts, namely part 20 which comprises positioning of the chip under the microscope, part 30 which consists of the system adjustments and part 40 which comprises the processing of information divided into two distinct sub-parts according to the embodiment chosen, either the PM mode or the CAMERA mode.

The chip positioning part 20 comprises, first of all a step 21 which consists of releasing the chip from its carrier; it is materially impossible to insert the entire chip under the microscope objective, that is to say both the microelectronic circuits and the carrier which is often a card of chip card type. The chip is therefore removed from its usual carrier and positioned on a more adapted carrier, namely an epoxy type carrier. This positioning is conducted manually with a certain amount of tolerance (in the region of 1/10 mm for example) due, in particular, to the irregularity existing between the epoxy carriers on which chips are fixed.

The chip is then blocked on an epoxy carrier by depression at step 23. After blocking the chip on this epoxy carrier, a step 24 consists of repositioning the carrier/chip unit under the optical axis of the microscope with misalignment in the region of one tenth of a millimetre. A step 25 consists subsequently of initialising the travelling stages along X and Y; in other words this consists of mechanically zeroing the travelling stages.

Part 30 entailing the system adjustments starts by step 31 which consists of choosing the field to be observed, then, at a stage 32, of focusing this field manually either with the eyepiece or on the camera image (the camera image being a white light image made using the ring illumination means).

The method continues with step 33 which consists of orienting the chip under the microscope. For reasons of simplicity, the chip is oriented in rotation manually using a control stage so that its axes are parallel to the absolute reference (i.e. to the optical axis connecting the objective and the camera or the photo multiplier). If necessary, this step can be automated using image analysis software calculating the orientation of the chip. This orientation can be made either by superimposing on the image a PC synthesised cross or by an optical method using light diffraction by the contacts.

The adjustment part is completed by step 34 to detect the origin which is made automatically. This step 34 consists of using image analysis software for automatic location of the first contact, that is to say the contact numbered "0". This "0" contact varies according to the numbering system chosen; it is often the contact placed on the top left of the contact matrix or else the central contact. This origin is located in relation to the optical centre (that is to say the intersection between the optical axis and the object plane) which enables control of travelling stages X and Y to bring the first contact, or contact 0 to the centre of the field.

The method for implementing the reader of the invention continues with information processing step 40, that is to say analysis of the fluorescence signal. This analysis step can be conducted using two different modes, either the PM mode or the CAMERA mode.

FIG. 2B gives a functional diagram of the PM mode. It is recalled that the PM mode is the embodiment implemented when the image acquisition means consist of a photo multiplier in conjunction with an acquisition circuit.

This embodiment is essentially used for routine analysis.

In this case, the image is not necessary which is why the camera can be replaced by a photo multiplier or a cooled avalanche photodiode which is markedly cheaper.

Also, with this embodiment, contact reading is automatic and sequential; the deflector system is therefore not necessarily of acoustic optical type.

The method of the invention, in this PM mode, consists first of all of a positioning step 51 to position the chosen contact, that is to say contact i, below the optic axis which may involve displacing the laser beam onto contact i.

Next step 52 consists of opening the shutter, followed by step 53 consisting of integrating onto the photo multiplier the signal received from contact i, then of memorising the signal obtained at step 54.

Step 55 consists of closing the shutter. The latter is of real advantage when movement is slow; it prevents all or part of the contact from being illuminated before stabilisation of the chip movement. In this case, the acquisition of the signal must be synchronised with the movements, that is to say the opening and closing of the shutter. Generally speaking, since the photo multiplier is an extremely sensitive light detector, the use of the shutter constitutes a very advantageous embodiment.

Step 56 consists of moving travelling stages X and Y in order to place the next contact under the objective and repeat the process.

When all the matrix contacts have been visualised, analysis of the fluorescence signal is made at step 57; in other words the fluorescence signal is used to determine the concentration of the substance under consideration mixed with the fluorophor. For persons skilled in the art this is a classical form of analysis and will not be described in this application.

FIG. 2C gives a functional diagram of the method of the invention in CAMERA mode.

For a more "fine-tuned" analysis of fluorescence, that is to say analysis which takes into consideration the homogeneity of the contact, a highly magnified image is preferably used for analysis, that is with a 10× or 20× objective. However with these objectives it is only possible to obtain a partial field (for example a 10× objective gives one quarter of the field).

This method starts by step 61 which consists of fitting the chosen objective lens to the microscope, that is a 5×, 10× or even 20× objective. The method continues with step 62 which consists of manual focus using the camera image.

Step 63 then consists of automatically positioning the sub-field on a sub-unit of contacts. This contact sub-unit is numbered according to the same principle as the one used for numbering the matrix contacts. The automatic positioning on a sub-unit of contacts is made using travelling stages X and Y.

Step 64 consists of scanning each sub-unit of contacts. This scanning is conducted using the acoustic optical deflector in over-sampled mode.

Step 65 consists of simultaneously integrating the signal on the camera. It can be specified, by way of example, that the beam is positioned on the edge of the contact to be scanned and that it scans this contact at a frequency of approximately 1 kHz while the camera integrates over a period of 100 $\mu$s to 10 s.

Finally step 66 consists of recording the images previously acquired and filing these images.

Also it is known to persons skilled in the art that the specificity of hybridisation is increased if the chip is heated in controlled manner. This is described in particular in the patent application filed in France under number 97 08864.

With the system of the invention, this heating can be made:
- either by globally heating the chip;
- or by localised heating per contact: this can be made with an electric resistance coiled around each contact; advantageously it can be obtained using the laser beam (preferably a visible pulsated laser) focused on the contact which it can heat without the need for any additional means.

What is claimed is:

1. System for determining the concentration of a substance mixed with a fluorophor and contained in one or more contacts of a matrix of contacts arranged on a scarcely absorbent, reflective carrier, characterised in that it comprises:
   a microscope (1), associated with a magnification objective lens (2) and image acquisition means (4,5) to obtain a microscope image of the fluorescence of one of the contacts of the matrix or of part of this contact;
   illumination means (11, 13) emitting a first beam to enable image acquisition in white light of said contact, and a second beam to excite the fluorophor contained in said contact;
   deflector means (15) to deflect the second beam and ensure point by point scanning of the contact of the matrix;
   recording means (6, 7) of the contact image; and
   processing means (6, 7) of this image to quantify the fluorescence of the contact and determine the concentration of the substance mixed with the fluorophor, using fluorescence intensity, illumination intensity and integration time on the image acquisition means.

2. System in accordance with claim 1, characterised in that the illumination means comprise a ring illumination source (11) which emits the first beam and a laser source (13) which emits the second beam.

3. System according to claim 2, characterised in that the laser is a micro laser.

4. System in accordance with claim 3, characterised in that the micro laser is a pulsated micro laser.

5. System in accordance with claim 1, characterised in that the image acquisition means comprise a cooled CCD camera, a colour filter placed in front of said camera and an electronic circuit ensuring the piloting of the camera and illumination means.

6. System according to claim 5, characterised in the colour filter is a high-pass filter.

7. System according to claim 1, characterised in that the image acquisition means comprise a photo multiplier associated with an acquisition circuit, a colour filter placed in front of said photo multiplier and an electronic circuit ensuring the piloting of the camera and illumination means.

8. System according to claim 1, characterised in that the microscope is fitted with a dichroic filter (3).

9. System according to claim 1, characterised in that the microscope operates by epi-illumination.

10. System according to claim 1, characterised in that the deflector means consist of an acoustic optical deflector deflecting the second beam in two orthogonal directions X and Y.

11. System according to claim 1, characterised in that the matrix is an electrically addressable matrix.

12. System according to claim 1, characterised in that the substance is made up of DNA strands hybridised to probes made from synthetic DNA.

13. System according to claim 12, characterised in that the DNA probes are strongly attached to the contacts using polypyrrol.

14. System according to claim 1, characterised in that the fluorophor is chosen from among the following products: phycoeryithrine, C-Snarf or sulphorhodamine.

15. System according to claim 1, which forms a small-sized reading box, characterised in that the matrix of contacts is carried by a card of chip card type.

16. Method for implementing the system according to claim 1, characterised in that it consists of:

a calibration step (20) of the system with positioning and blocking of the matrix under the optical axis of the microscope objective, focusing the image acquisition means, and automatic search of a reference contact in relation to the optical centre of the system;

an image acquisition step (30) of one contact of the matrix; and a calculation step (40) to calculate the fluorescence of said contact then deducting the concentration of the substance.

17. Method according to claim 16, in which image acquisition is made with a cooled CCD camera, characterised in that it comprises, between the calibration and acquisition steps, a scanning step in which the contact under consideration is scanned point by point.

* * * * *